US012053160B2

(12) United States Patent
Kimura et al.

(10) Patent No.: US 12,053,160 B2
(45) Date of Patent: Aug. 6, 2024

(54) ENDOSCOPY SUPPORT APPARATUS, ENDOSCOPY SUPPORT METHOD, AND COMPUTER READABLE RECORDING MEDIUM

(71) Applicant: NEC Corporation, Tokyo (JP)

(72) Inventors: Tatsu Kimura, Tokyo (JP); Kenichi Kamijo, Tokyo (JP); Shota Ohtsuka, Tokyo (JP); Kimiyasu Takoh, Tokyo (JP); Ikuma Takahashi, Tokyo (JP); Motoyasu Okutsu, Tokyo (JP)

(73) Assignee: NEC CORPORATION, Tokyo (JP)

( * ) Notice: Subject to any disclaimer, the term of this patent is extended or adjusted under 35 U.S.C. 154(b) by 201 days.

(21) Appl. No.: 17/635,786

(22) PCT Filed: Jan. 10, 2020

(86) PCT No.: PCT/JP2020/000647
§ 371 (c)(1),
(2) Date: Feb. 16, 2022

(87) PCT Pub. No.: WO2021/140644
PCT Pub. Date: Jul. 15, 2021

(65) Prior Publication Data
US 2022/0287550 A1 Sep. 15, 2022

(51) Int. Cl.
*A61B 1/045* (2006.01)
*A61B 1/00* (2006.01)
*G06T 7/00* (2017.01)

(52) U.S. Cl.
CPC ........ *A61B 1/045* (2013.01); *A61B 1/000094* (2022.02); *G06T 7/0012* (2013.01);
(Continued)

(58) Field of Classification Search
CPC . A61B 1/045; A61B 1/000094; G06T 7/0012; G06T 2207/10068; G06T 2207/30096
(Continued)

(56) References Cited

U.S. PATENT DOCUMENTS 11,450,425 B2 * 9/2022 Kamon ............ A61B 1/000094
2016/0302644 A1 * 10/2016 Umemoto .......... A61B 1/00148
(Continued)

FOREIGN PATENT DOCUMENTS

CN   112399816 A * 2/2021 ......... A61B 1/00006
CN   113164010 A * 7/2021 ....... A61B 1/000094
(Continued)

OTHER PUBLICATIONS

English translation of Written opinion for PCT Application No. PCT/JP2020/000647, dated Jul. 21, 2022.
(Continued)

*Primary Examiner* — John W Miller
*Assistant Examiner* — Omer Khalid

(57) ABSTRACT

An endoscopy support apparatus 1 includes: an analysis information generation unit 2 that inputs image information of an imaged living body into a model, estimates a region of a target site of the living body, and generates analysis information including region information indicating the estimated region and score information indicating likeness of the region to the target site; a user information generation unit 3 that generates user information related to the user, which has been input by a user using a user interface 23; an image-related information generation unit 4 that generates image-related information by associating imaging date and time information, the analysis information, and the user information, for each piece of image information; and an examination management information generation unit 5 that generates examination management information by associ- (Continued)

ating a plurality of pieces of the image-related information with examination information indicating an examination period.

15 Claims, 11 Drawing Sheets

(52) U.S. Cl.
 CPC ............... *G06T 2207/10068* (2013.01); *G06T 2207/30096* (2013.01)

(58) Field of Classification Search
 USPC .......................................................... 348/65
 See application file for complete search history.

(56) References Cited

U.S. PATENT DOCUMENTS

| | | | |
|---|---|---|---|
| 2019/0192048 A1 | 6/2019 | Makino et al. | |
| 2019/0380617 A1* | 12/2019 | Oosake | A61B 1/00006 |
| 2020/0126655 A1* | 4/2020 | Sasaki | A61B 1/00009 |
| 2020/0242766 A1* | 7/2020 | Endo | A61B 1/0638 |

FOREIGN PATENT DOCUMENTS

| | | |
|---|---|---|
| EP | 3590415 A1 | 1/2020 |
| JP | 2008-079648 A | 4/2008 |
| JP | 2016-221065 A | 12/2016 |
| JP | 2017-056123 A | 3/2017 |
| WO | 2018/043550 A1 | 3/2018 |
| WO | 2018/159461 A1 | 9/2018 |
| WO | 2018/221033 A1 | 12/2018 |
| WO | 2018/235420 A1 | 12/2018 |
| WO | 2019/078102 A1 | 4/2019 |

OTHER PUBLICATIONS

International Search Report for PCT Application No. PCT/JP2020/000647, dated Mar. 17, 2020.
Extended European Search Report for EP Application No. 20912344.7, dated Feb. 23, 2023.

* cited by examiner

Fig. 5

| IMAGE INFORMATION | IMAGING DATE AND TIME INFORMATION | ANALYSIS INFORMATION | | USER INFORMATION |
|---|---|---|---|---|
| | | REGION INFORMATION | SCORE INFORMATION | |
| image_1 | 2019/11/10/11:20:34:120 | area_1 | score_1 | user_1 |
| image_2 | 2019/11/10/11:20:34:121 | area_2 | score_2 | |
| image_3 | 2019/11/10/11:20:34:122 | area_3 | score_3 | |
| ... | ... | ... | ... | |

| EXAMINATION INFORMATION | IMAGE INFORMATION | IMAGING DATE AND TIME INFORMATION | ANALYSIS INFORMATION | | USER INFORMATION |
|---|---|---|---|---|---|
| | | | REGION INFORMATION | SCORE INFORMATION | |
| check_1 | image_1 | 2019/11/10/11:20:34:120 | area_1 | score_1 | user_1 |
| | image_2 | 2019/11/10/11:20:34:121 | area_2 | score_2 | |
| | image_3 | 2019/11/10/11:20:34:122 | area_3 | score_3 | |
| | ... | ... | ... | ... | |
| | image_XXXXXX | 2019/11/10/11:20:55:100 | area_XXXXXX | score_XXXXXX | |

71

ENDOSCOPY SUPPORT APPARATUS, ENDOSCOPY SUPPORT METHOD, AND COMPUTER READABLE RECORDING MEDIUM

This application is a National Stage Entry of PCT/JP2020/000647 filed on Jan. 10, 2020, the contents of all of which are incorporated herein by reference, in their entirety.

TECHNICAL FIELD

The technical field relates to an endoscopy support apparatus and an endoscopy support method that support endoscopy, and further relates to a computer readable recording medium on which a program for realizing them is recorded.

BACKGROUND ART

When a user performs an examination, an endoscopy system obtains a large amount of image information captured by an endoscope, performs image analysis on each obtained piece of image information, and uses the image information and image analysis results to present a living body internal image and the image analysis results to the user. However, in the endoscopy system, the living body internal image and the image analysis results can be displayed on a display of a display device in real time during the examination, but a large amount of image information and the image analysis results are not organized and are stored in a storage device in a complicated manner.

As a related technique, Patent Document 1 discloses a medical image data processing system for efficiently using medical image data. According to the medical image data processing system of Patent Document 1, the medical image data is managed by storing the medical image data and management information indicating the contents of the medical image data. Note that the management information is, for example, a management number of the medical image data, a modality type, imaging date and time, a patient name, a user name (a doctor name or an imaging engineer), an imaging site, imaging conditions, a reference image number, and the like.

LIST OF RELATED ART DOCUMENTS

Patent Document

Patent Document 1: Japanese Patent Laid-Open Publication No. 2008-079648

SUMMARY

Technical Problems

However, the medical image data processing system of Patent Document 1 is not a system that organizes and manages a large amount of obtained image information for each examination. Further, the medical image data processing system of Patent Document 1 is not an apparatus that performs image analysis on each piece of a large amount of obtained image information.

Furthermore, since the conventional endoscopy system is assumed to be used continuously by a plurality of users, it is desired that a large number of living body internal images obtained during an examination period and the image analysis results are organized for each examination so that the user can efficiently use them.

An example object of the invention is to provide an endoscopy support apparatus and an endoscopy support method that organize a large number of biological images obtained during the examination period and the image analysis results for each examination, and a computer readable recording medium.

Solution to the Problems

In order to achieve the above object, an endoscopy support apparatus in one aspect of the present invention includes:
an analysis information generation unit that inputs image information of an imaged living body into a model, estimates a region of a target site of the living body, and generates analysis information including region information indicating the estimated region and score information indicating likeness of the region to the target site;
a user information generation unit that generates user information related to a user, which has been input by the user using a user interface;
an image-related information generation unit that generates image-related information by associating imaging date and time information indicating a date and time when an image was captured, the analysis information, and the user information, for each piece of image information; and
an examination management information generation unit that generates examination management information by associating a plurality of pieces of the image-related information generated during an examination period with examination information indicating examination.

Further, in order to achieve the above object, an endoscopy support method in one aspect of the present invention includes:
inputting image information of an imaged living body into a model, estimating a region of a target site of the living body, and generating analysis information including region information indicating the estimated region and score information indicating likeness of the region to the target site;
generating user information related to a user, which has been input by the user using a user interface;
generating image-related information by associating imaging date and time information indicating a date and time when an image was captured, the analysis information, and the user information, for each piece of image information; and
generating examination management information by associating a plurality of pieces of the image-related information with examination information indicating an examination period.

Further, in order to achieve the above object, a computer readable recording medium in one aspect of the present invention includes a program recorded thereon, the program including instructions that cause a computer to carry out:
inputting image information of an imaged living body into a model, estimating a region of a target site of the living body, and generating analysis information including region information indicating the estimated region and score information indicating likeness of the region to the target site;
generating user information related to a user, which has been input by the user using a user interface;
generating image-related information by associating imaging date and time information indicating a date and time when an image was captured, the analysis information, and the user information, for each piece of image information; and generating examination management information by associating a plurality of pieces of the image-related information with examination information indicating an examination period.

Advantageous Effects of the Invention

As described above, according to the present invention, it is possible to organize a large number of biological images obtained during the examination period and the image analysis results, for each examination.

BRIEF DESCRIPTION OF THE DRAWINGS

FIG. 5 is a diagram for describing an example of a data structure of image-related information.

FIG. 7 is a diagram for describing an example of a data structure of examination management information.

EXAMPLE EMBODIMENT

Example Embodiment

Hereinafter, an example embodiment of the present invention will be described with reference to FIGS. 1 to 11.

[Apparatus Configuration]

Figure 1:
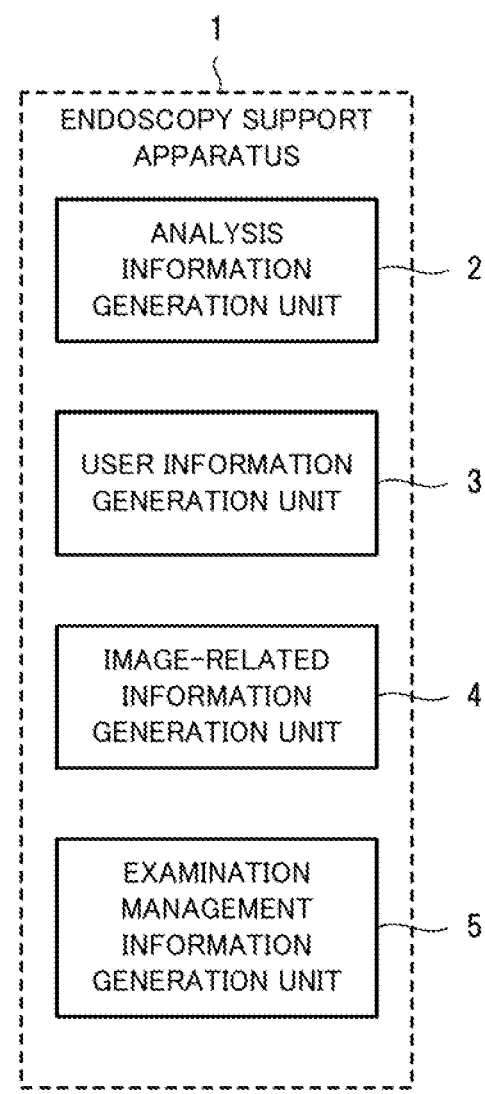
FIG. 1 is a diagram for describing an example of an endoscopy support apparatus.

First, a configuration of an endoscopy support apparatus in the present example embodiment will be described with reference to FIG. 1. FIG. 1 is a diagram for describing an example of the endoscopy support apparatus.

An endoscopy support apparatus 1 is an apparatus for organizing a large number of living body internal images obtained during an examination period and image analysis results thereof. The endoscopy support apparatus 1 is, for example, an information processing apparatus such as a personal computer or a server computer. As illustrated in FIG. 1, the endoscopy support apparatus 1 includes an analysis information generation unit 2, a user information generation unit 3, an image-related information generation unit 4, and an examination management information generation unit 5.

The analysis information generation unit 2 inputs image information of an imaged living body to a model, estimates a region of a target site of the living body, and generates analysis information including region information indicating the estimated region, and score information indicating likeness of the region to the target site.

The image information is information indicating, for example, a biological image of an internal or external organ of a living body, such as a human, an animal, or a plant, captured by an imaging device mounted on an endoscope. The target site is, for example, a region with a lesion or an abnormality. The region information is a region estimated to be the target site included in the biological image captured by the endoscope. The score information is an index indicating a degree (or a probability) that the region estimated to be the target site is estimated to be the lesion or the abnormality.

The model is a model generated by artificial intelligence (AI), machine learning, or the like. The model may be provided, for example, in the endoscopy support apparatus 1 or outside the endoscopy support apparatus 1.

The user information generation unit 3 generates user information related to a user, which is input by the user using a user interface. The image-related information generation unit 4 generates image-related information by associating imaging date and time information indicating a date and time when the image was captured, the analysis information, and the user information, for each piece of image information. The examination management information generation unit 5 generates examination management information by associating a plurality of pieces of image-related information with examination information indicating the examination period.

As described above, in the present example embodiment, since the image-related information including the image information, the analysis information, and the user information can be managed for an examination, the user can efficiently use the image information and the analysis information after the examination.

[System Configuration]

Figure 2:
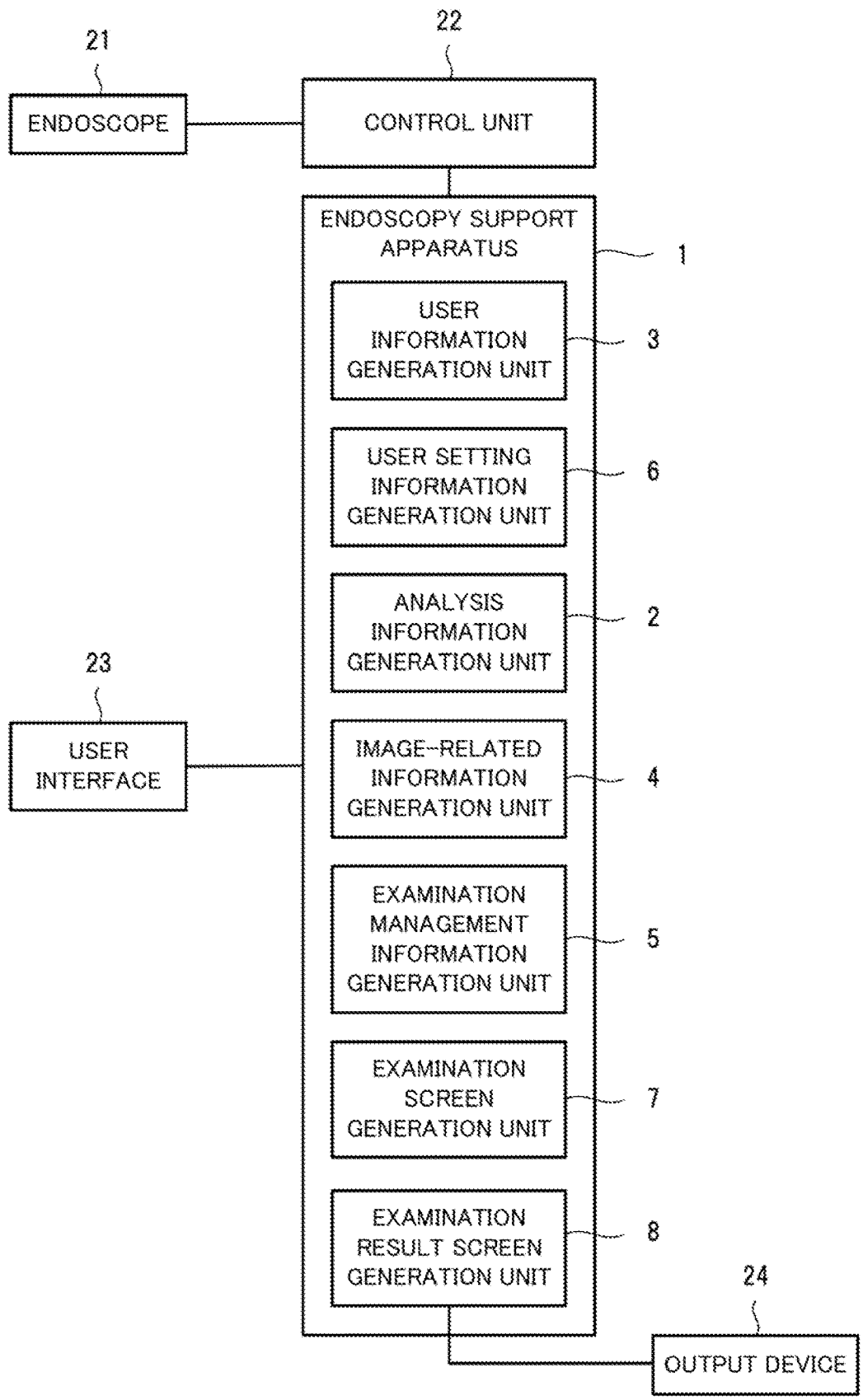
FIG. 2 is a diagram for describing an example of a system including the endoscopy support apparatus.

Subsequently, the configuration of the endoscopy support apparatus 1 in the present example embodiment will be described more specifically with reference to FIG. 2. FIG. 2 is a diagram for describing an example of a system including the endoscopy support apparatus.

As illustrated in FIG. 2, a system 20 including the endoscopy support apparatus 1 in the present example embodiment includes an endoscope 21, a control unit 22, a user interface 23, and an output device 24 in addition to the endoscopy support apparatus 1. Further, the endoscopy support apparatus 1 includes a user setting information generation unit 6, an examination screen generation unit 7, and an examination result screen generation unit 8 in addition to the analysis information generation unit 2, the user information generation unit 3, the image-related information generation unit 4, and the examination management information generation unit 5.

The endoscope 21 transmits an image of the inside of the living body, which is obtained by imaging the inside of the living body, to the control unit 22 connected to the endoscope 21. The endoscope 21 includes, for example, an insertion portion to be inserted inside the living body, an imaging device such as a camera provided on a tip side of the insertion portion, an operating unit that operates curvature of the insertion portion, imaging of an imaging unit, and the like, and a connection portion that connects the endoscope 21 and the endoscopy support apparatus 1. Further, in addition to the imaging device, the endoscope 21 includes a lighting unit, a nozzle used for air supply, water supply, and suction, a forceps mouth, and the like on the tip side of the insertion portion.

The control unit 22 is, for example, a video processor or the like that performs image processing or the like on the input image. Specifically, the control unit 22 obtains an imaging signal from the endoscope 21, performs image adjustment or the like on the imaging signal, generates the image obtained by imaging the inside of the living body, and outputs it to the endoscopy support apparatus 1. Note that the control unit 22 may be provided in the endoscopy support apparatus 1.

The user interface 23 is an input screen or the like displayed on a display of the output device 24 when the user inputs information. Further, the user inputs information through the user interface 23 using an operating device. Specifically, the user inputs information using a visual element (graphical information) displayed on the display, a keyboard, a mouse, a touch panel, or the like.

The output device 24 outputs images, sounds, and the like. The output device 24 is, for example, an image display device including liquid crystal, organic electroluminescence (EL), and a cathode ray tube (CRT). Further, the output device 24 includes an audio output device or the like such as a speaker. Note that the output device 24 may be a printing device such as a printer.

The endoscopy support apparatus will be described in detail. The user information generation unit 3 generates the user information on the basis of the information related to the user input by the user using the user interface 23. The user information may include identification information for identifying the user to be examined, gender information indicating a gender of the user, age information indicating an age of the user, job title information indicating a job title of the user, experience information indicating an experience value and years of experience of the user, name recognition information indicating name recognition of the user, evaluation information indicating evaluation of the user, and the like. However, the user information is only required to include the identification information and any one or more pieces of information described above other than the identification information.

Specifically, first, the user information generation unit 3 displays the user interface 23 for inputting the information related to the user on the display of the output device 24. Subsequently, the user information generation unit 3 generates the user information on the basis of the information related to the user, which has been input through the user interface 23. Subsequently, the user information generation unit 3 stores the user information in the storage device.

The user setting information generation unit 6 generates user setting information (a profile) used for setting output of the analysis information for each user. The user setting information includes at least one of setting information for changing display of the region according to the score information and setting information for changing a volume according to the score information, in the examination.

Specifically, first, the user setting information generation unit 6 displays a user setting information generation screen as the user interface on the display of the output device 24. Subsequently, the user setting information generation unit 6 obtains the information input by the user by using the user setting information generation screen. Subsequently, the user setting information generation unit 6 generates the user setting information using the obtained information, and stores the user setting information in the storage device. The user setting information generation screen is, for example, a screen as illustrated in FIG. 3.

Figure 3:
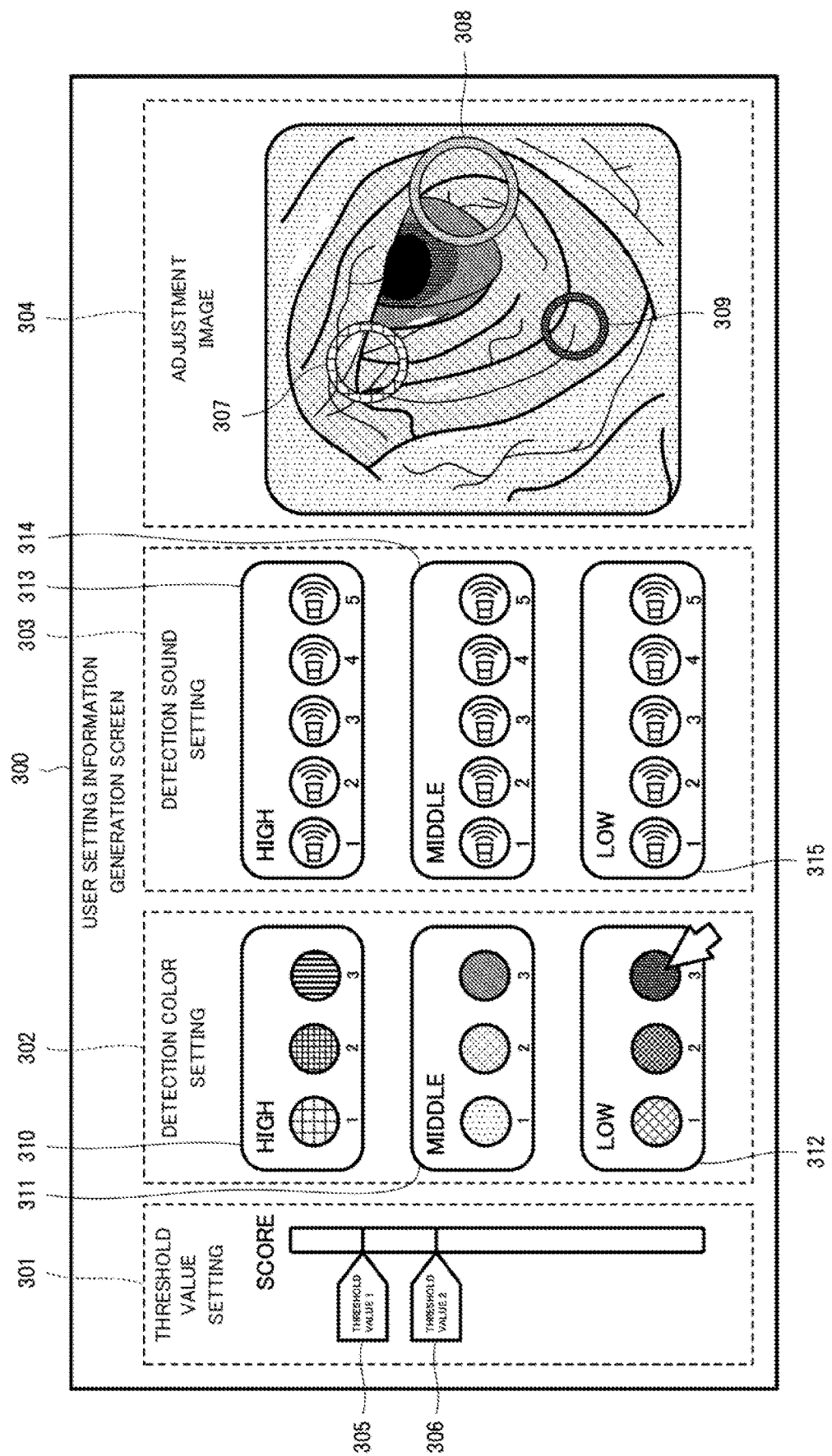
FIG. 3 is a diagram for describing an example of a user setting information generation screen.

FIG. 3 is a diagram for describing an example of the user setting information generation screen. On a user setting information generation screen 300 illustrated in FIG. 3, a threshold setting unit 301, a detection color setting unit 302, a detection sound setting unit 303, and an adjustment screen 304 are displayed.

The threshold setting unit 301 sets a threshold value used to divide a score into a plurality of ranges. In the example of FIG. 3, there is provided a control bar including a scale display 305 for setting a threshold value 1 and a scale display 306 for setting a threshold value 2 in order to determine three score ranges of "HIGH", "MIDDLE", and "LOW". In the example of FIG. 3, the user can change the threshold value by moving the scale displays 305 and 306 of the control bar up and down.

The scale display 305 is used to determine a lower limit of the score range corresponding to "HIGH" or an upper limit of the score range corresponding to "MIDDLE". The scale display 306 is used to determine a lower limit of the score range corresponding to "MIDDLE" or an upper limit of the score range corresponding to "LOW". Further, the set scores are displayed in the threshold values 1 and 2 in FIG. 3.

However, the score range is not limited to the three ranges. Further, in the example of FIG. 3, the control bar is used for adjusting the threshold values, but adjustment of the threshold values is not limited to the control bar, and another input method may be employed.

The detection color setting unit 302 is used to set a color of a detection range display used to make the region of the detected target site easy for the user to understand. The detection color setting unit 302 is used for setting to change the color of the detection range display according to the score corresponding to the region of the detected target site when the region of the target site is detected.

The detection range display is displayed as 307, 308, and 309 on the adjustment screen 304 of FIG. 3. In FIG. 3, a difference in color is represented by a difference in pattern.

Further, in the example of FIG. 3, since the three score ranges of "HIGH", "MIDDLE", and "LOW" are set, a HIGH color setting display 310, a MIDDLE color setting display 311, and a LOW color setting display 312 are used to set colors corresponding to the three score ranges of "HIGH", "MIDDLE", and "LOW".

In the case of the HIGH color setting display 310, the color is set by causing the user to select one of three color circular displays (1 to 3) displayed on the HIGH color setting display 310. Note that in FIG. 3, the difference in color is represented by the difference in pattern. The colors of the MIDDLE color setting display 311 and the LOW color setting display 312 are also set as described above. However, the types of the colors are not limited to three.

The detection range displays 307, 308, and 309 are donut-shaped on the adjustment screen 304 of FIG. 3, but are not limited to the donut shape. For example, the shape may extend along the region. That is, the display is only required to be such that the region of the target site can be easily understood by the user.

The detection sound setting unit 303 is used to set the volume used to make it easy for the user to understand that the region of the target site has been detected. The detection sound setting unit 303 is used for setting to change the volume according to the score corresponding to the region of the detected target site when the region of the target site is detected.

In the example of FIG. 3, since the three score ranges of "HIGH", "MIDDLE", and "LOW" are set, a HIGH sound setting display 313, a MIDDLE sound setting display 314, and a LOW sound setting display 315 are used to set volumes corresponding to the three score ranges of "HIGH", "MIDDLE", and "LOW".

In the case of the HIGH sound setting display 313, the volume is set by causing the user to select one of five volume displays (1 to 5) displayed on the HIGH sound setting display 313 together with the sound corresponding to HIGH. Note that in FIG. 3, the larger the number, the louder the volume. The volumes of the MIDDLE sound setting display 314 and the LOW sound setting display 315 are also set as described above. However, the types of volumes are not limited to five.

Further, a detection sound may be a sound that differs depending on the score range. Further, the detection sound may be, for example, a sound such as music, a buzzer sound, or a voice.

The adjustment screen 304 is a screen referred to by the user when the above-mentioned threshold setting, detection color setting, and detection sound setting are performed. Specifically, the adjustment screen 304 is a screen used by the user to refer to an adjustment image, change each setting, and select a setting that is easy for the user to use.

The analysis information generation unit 2 analyzes the image information of the imaged living body and generates the analysis information. The analysis information includes the region information indicating the region of the target site (the target site image) and the score information indicating the likeness to the target site.

Specifically, first, the analysis information generation unit 2 obtains from the control unit 22 the image information generated by the control unit 22 using the imaging signal output from the endoscope 21. Subsequently, the analysis information generation unit 2 inputs the image information into the model and obtains the analysis information (the region information and the score information) output from the model. Subsequently, the analysis information generation unit 2 outputs the analysis information to the image-related information generation unit 4 and the examination screen generation unit 7.

When the image-related information generation unit 4 obtains start information indicating start of the examination, the image-related information generation unit 4 generates the image-related information by associating the imaging date and time information, the analysis information, and the user information, for each piece of image information. Note that information other than the imaging date and time information, the analysis information, and the user information may be associated with the image information.

Figure 4:
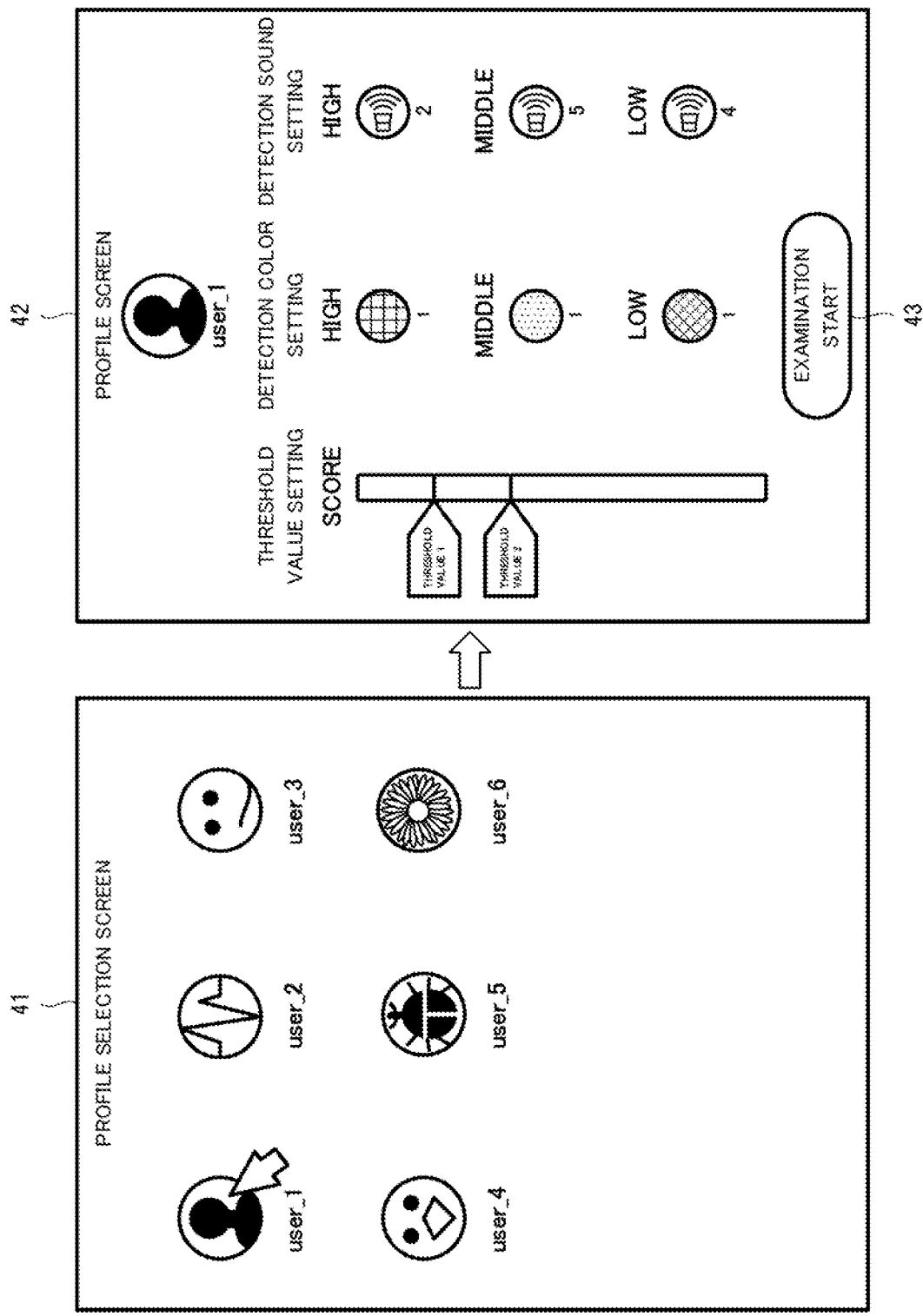
FIG. 4 is a diagram for describing an example of a profile selection screen and a profile screen.

FIG. 4 is a diagram for describing an example of a profile selection screen and a profile screen. For example, the examination screen generation unit 7 displays on the display of the output device 24 a profile selection screen 41 as illustrated in FIG. 4, as the user interface. Subsequently, when an icon corresponding to the profile to be used is selected by the user, a profile screen 42 displaying contents of a preset profile corresponding to the selected icon is displayed on the display.

Specifically, when an icon "user_1" of the profile selection screen 41 is selected by the user in FIG. 4, the preset profile screen 42 corresponding to the icon "user_1" is displayed. Subsequently, when the user determines that the examination is to be started with the contents displayed on the profile screen 42, an examination start display 43 is selected by the user, and the start information is output to the image-related information generation unit 4.

Note that the profile selection screen 41 may display an icon that can be shared and used by the user. For example, an icon associated with a profile of a well-known doctor, an icon associated with a profile produced according to the race, gender, and age of a patient, and the like are conceivable.

Subsequently, the image-related information generation unit 4 generates the image-related information by associating the imaging date and time information, the analysis information (the region information and the score information) corresponding to the image information output from the model, and the user information, for each piece of image information input to the model included in the analysis information generation unit 2. The image-related information is, for example, information illustrated in FIG. 5.

FIG. 5 is a diagram for describing an example of a data structure of the image-related information. "Image_1", "image_2", "image_3", . . . of the "image information" illustrated in FIG. 5 indicate, for example, file names of the image information. "2019/11/10/11:20:34:120", "2019/11/10/11:20:34:121", "2019/11/10/11:20:34:122", . . . of the "imaging date and time information" illustrated in FIG. 5 indicate, for example, the date and time (year, month, day, time) when the image was captured. "Area_1", "area_2", "area_3", . . . of the "region information" in the "analysis information" illustrated in FIG. 5 are, for example, coordinates for indicating at least one region of a lesion or an abnormality, on the image. "Score_1", "score_2", "score_3", . . . of the "score information" in the "analysis information" illustrated in FIG. 5 are, for example, indices indicating degrees (or probabilities) that a detected tumor region is a tumor region when a tumor is detected as a lesion in the image.

Note that the image-related information generation unit 4 may further generate the image-related information by associating order information indicating the order in which the images were captured in the examination with the image information.

Further, the image-related information may be associated with capture information indicating that the user captured the image using the endoscope. Thus, the user can easily view the captured image after the examination. Note that examples of a capture detection method include a method of detecting a preset number of the same image (or images with little change), a method of continuously detecting the same image for a preset period, and a method of detecting that a snapshot has been generated.

Further, the image-related information may be associated with adjustment history information indicating that adjustment of the color and volume of the detection range display performed by the user during the examination was performed.

When the examination management information generation unit 5 obtains end information indicating an end of the examination, the examination management information generation unit 5 generates the examination management information for managing the examination by associating the examination information indicating the examination period with the plurality of pieces of image-related information generated during the examination period.

Figure 6:
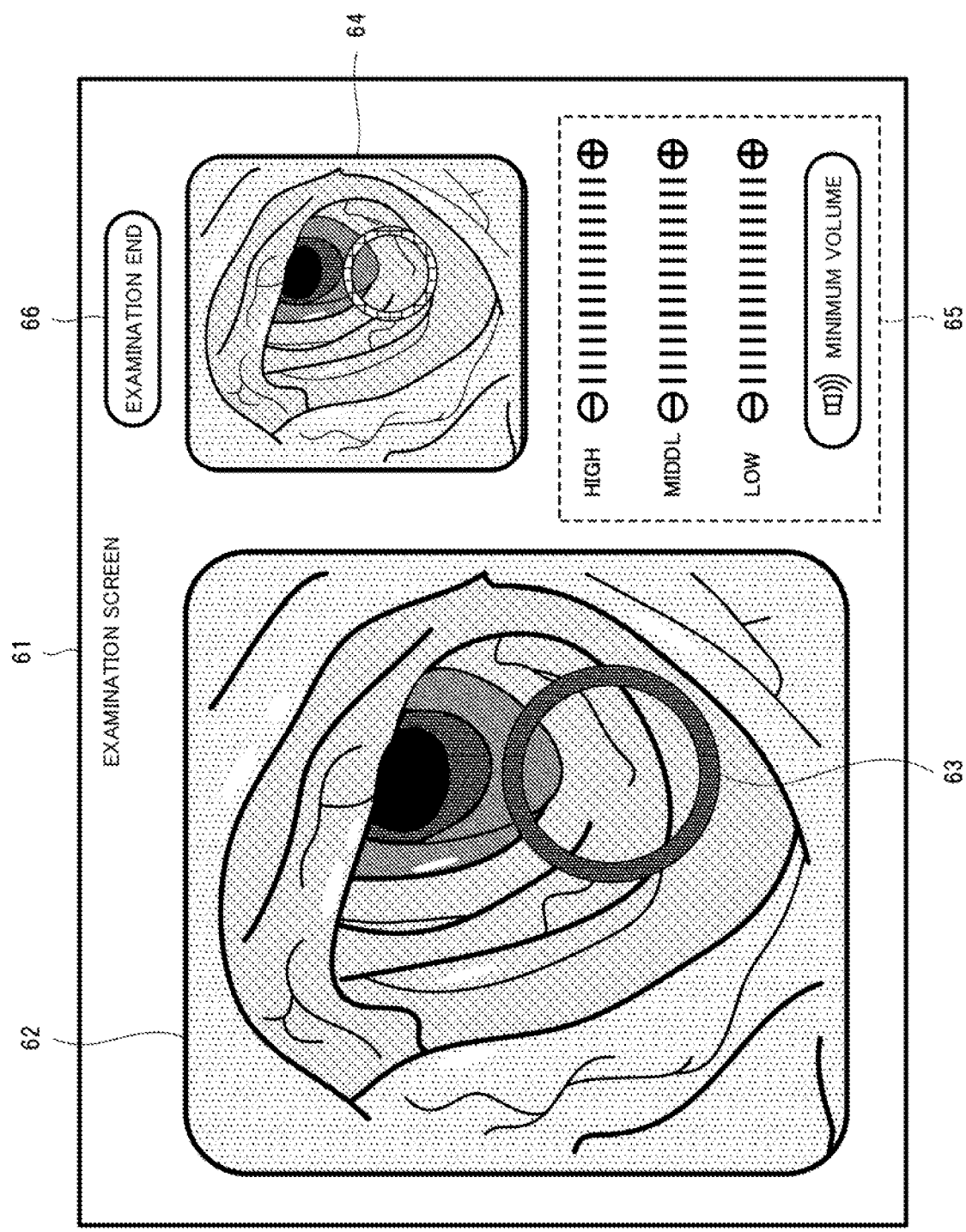
FIG. 6 is a diagram for describing an example of an examination screen.

Specifically, first, the examination management information generation unit 5 obtains the end information indicating the end of the examination. FIG. 6 is a diagram for describing an example of an examination screen. For example, the examination screen generation unit 7 displays an examination screen 61 as illustrated in FIG. 6 as the user interface on the display of the output device 24.

In the example of FIG. 6, the examination screen 61 displays an image display 62 for displaying the image of the living body and a detection range display 63 for displaying the region of the target site of the image display 62. In addition, there are displayed a color adjustment unit 64 for adjusting the color of the detection range display during the examination, a volume adjustment unit 65 for adjusting the volume during the examination, and an examination end display 66 for the user to select when the examination is completed.

When the user determines that the examination is completed, the examination end display 66 is selected by the user, and the end information is output to the examination management information generation unit 5. Subsequently, the examination management information generation unit 5 generates the examination management information by associating the plurality of pieces of image-related information generated during the examination period with the examination information indicating a period during which the examination is currently being performed. Subsequently, the examination management information generation unit 5 stores the generated examination management information in the storage device. The examination management information is, for example, information as illustrated in FIG. 7.

FIG. 7 is a diagram for describing an example of a data structure of the examination management information. "Check_1" of the "examination information" illustrated in FIG. 7 is information for identifying the examination performed by the user. In the example of FIG. 7, in the examination of "check_1", "image_XXXXXX" is obtained from "image_1" as the image information, and the related information is associated with each piece of image information obtained.

In addition, in FIG. 7, the region information and the score information are associated with all of the image information, but when the target site is not detected, information is stored indicating that there is no data in the region information and the score information.

Thus, the image-related information can be managed for each examination, and therefore the user can efficiently use the image information and the analysis information after the examination.

The examination screen generation unit 7 generates output information for outputting the examination screen (the image, the sound, and the like) to the output device 24 on the basis of the image information, the analysis information, and the user setting information. Specifically, the examination screen generation unit 7 generates the output information for displaying the examination screen 61 as illustrated in FIG. 6 on the display of the output device 24. Further, the examination screen generation unit 7 generates the output information for output from the speaker of the output device 24.

Note that when the user is a doctor and shows and explains the examination screen to the patient during the examination, in order to make the color easy for the patient to understand, the user changes the color by using the color adjustment unit 64. Further, when the sound is not required in the case of explanation, the volume adjustment unit 65 is used to minimize the volume.

Figure 8:
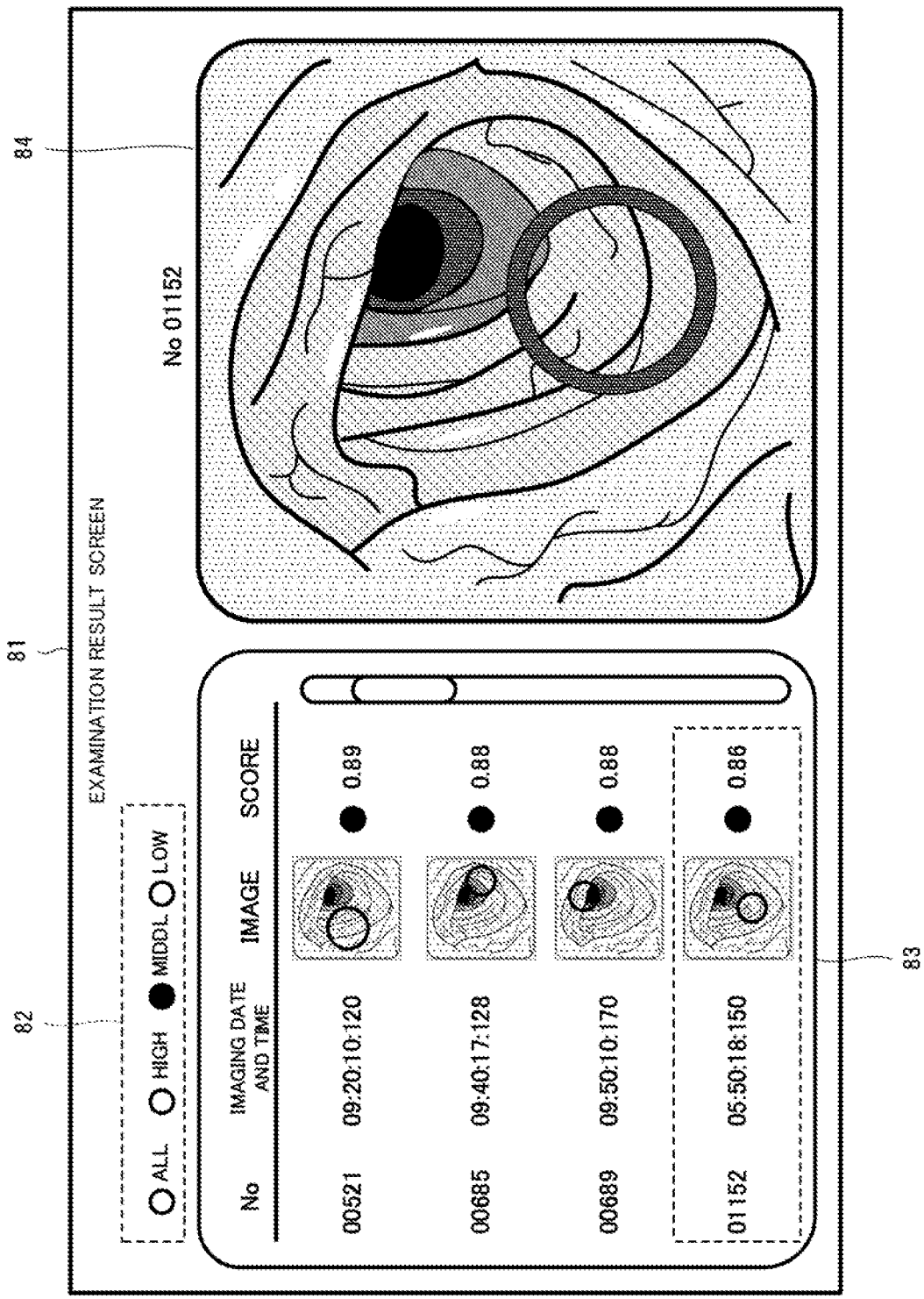
FIG. 8 is a diagram for describing an example of an examination result screen.

The examination result screen generation unit 8 obtains the examination management information from the storage device, and outputs the image, the sound, and the like to the output device 24. FIG. 8 is a diagram for describing an example of the examination result screen. The examination result screen generation unit 8 generates the output information for displaying, for example, an examination result screen 81 as illustrated in FIG. 8 on the display of the output device 24. Further, the examination result screen generation unit 8 generates, for example, the output information for output from the speaker of the output device 24.

In the example of FIG. 8, the examination result screen 81 includes a filter unit 82 that classifies and displays the image and the analysis result according to the score information associated with the image information. Further, in the example of FIG. 8, since "MIDDLE" is selected (black circle) by the user in the filter unit 82, the image associated with the score included in the score range of "MIDDLE", the imaging date and time, and the score are displayed in a related information display unit 83. Note that if "ALL" is selected, all of the images can be referred to. Further, in the example of FIG. 8, an examination result display unit 84 displays an examination result image corresponding to "01152" selected by the user by using the related information display unit 83.

Note that after the examination is completed, the adjustment made during the examination may be fed back to automatically change profile settings. For example, the profile setting may be changed on the basis of the adjustment history information included in the image-related information described above.

[Apparatus Operation]

Figure 9:
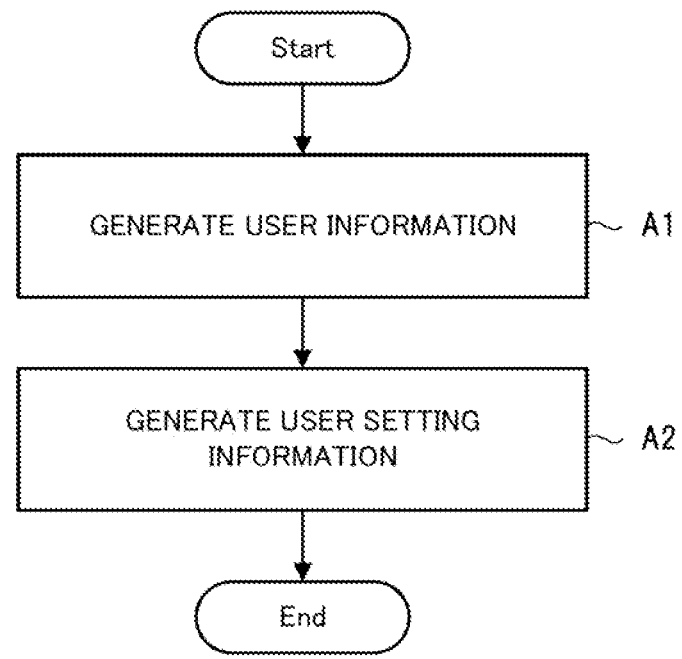
FIG. 9 is a diagram for describing an operation example of the endoscopy support apparatus.
Figure 10:
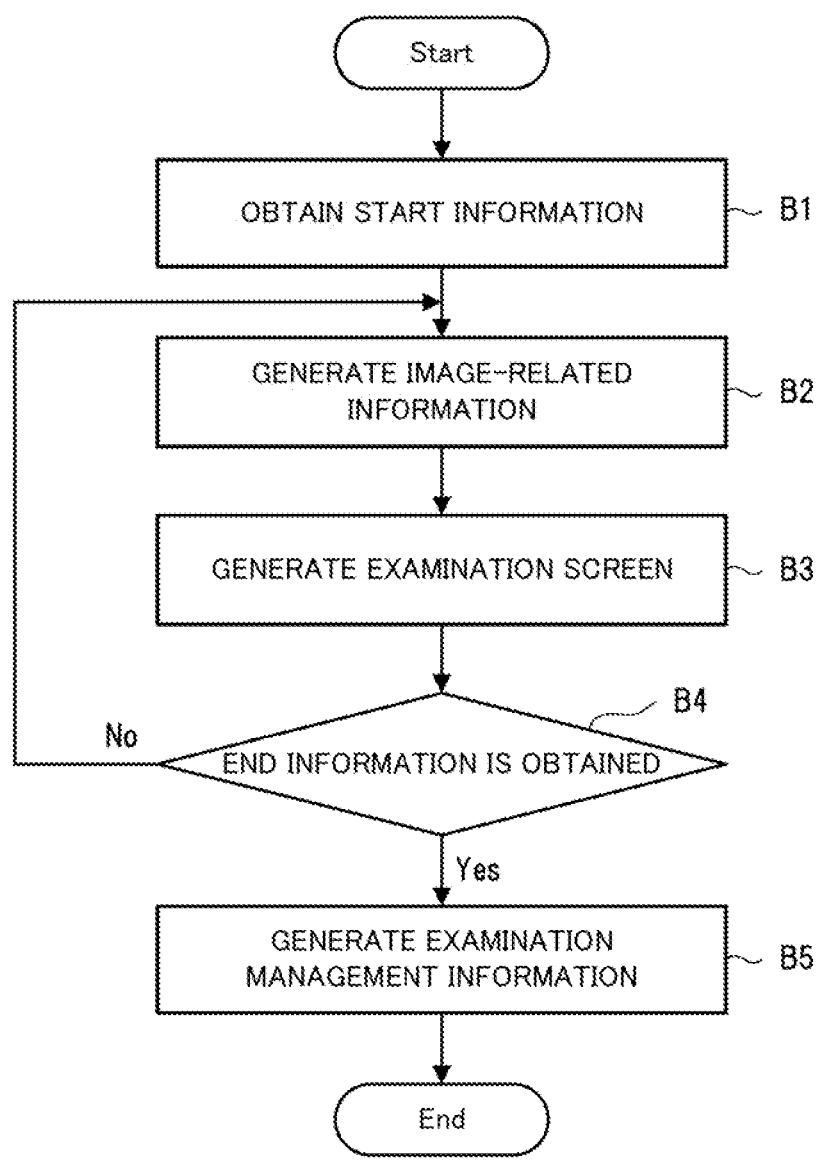
FIG. 10 is a diagram for describing an operation example of the endoscopy support apparatus.

Next, an operation of the endoscopy support apparatus in an example embodiment of the present invention will be described with reference to FIGS. 9 and 10. FIGS. 9 and 10 are diagrams for describing an operation example of the endoscopy support apparatus. In the following description, FIGS. 1 to 8 will be referred to as appropriate. Further, in the present example embodiment, an endoscopy support method is implemented by operating the endoscopy support apparatus. Therefore, description of the endoscopy support method in the present example embodiment is replaced with the following operation description of the endoscopy support apparatus.

Settings before the examination will be described.

As illustrated in FIG. 9, first, the user information generation unit 3 generates the user information related to the user, which has been input by the user using the user interface 23 (step A1).

Specifically, in step A1, first, the user information generation unit 3 displays the user interface 23 for inputting the information related to the user on the display of the output device 24. Subsequently, in step A1, the user information generation unit 3 obtains the user information input through the user interface 23. Subsequently, in step A1, the user information generation unit 3 stores the user information in the storage device.

Subsequently, the user setting information generation unit 6 generates the user setting information (the profile) used for setting the output of the analysis information for each user (step A2).

Specifically, in step A2, first, the user setting information generation unit 6 displays the user setting information generation screen as the user interface on the display of the output device 24. Subsequently, in step A2, the user setting information generation unit 6 obtains the information input by the user using the user setting information generation screen. Subsequently, in step A2, the user setting information generation unit 6 generates the user setting information using the obtained information, and stores the user setting information in the storage device.

The operation during the examination will be described.

As illustrated in FIG. 10, first, the image-related information generation unit 4 obtains the start information indicating the start of the examination (step B1).

Specifically, when the icon of the profile selection screen 41 displayed on the display of the output device 24 is selected by the user, the profile corresponding to the selected icon is displayed on the profile screen 42. Subsequently, when the user determines that the examination is to be started with the contents displayed on the profile screen 42, the examination start display 43 is selected by the user, and the start information is output to the image-related information generation unit 4.

Subsequently, the image-related information generation unit 4 generates the image-related information by associating the imaging date and time information, the analysis information, the user information, and the like, for each piece of image information (step B2).

Specifically, in step B2, the image-related information generation unit 4 generates the image-related information by associating the imaging date and time information indicating the date and time when the image was captured, the analysis information (the region information and the score information) corresponding to the image information output from the model, and the user information, for each piece of image information input to the model included in the analysis information generation unit 2. The image-related information is, for example, the information illustrated in FIG. 5.

Note that the image-related information generation unit 4 may further generate the image-related information by associating the order information indicating the order in which the images were captured in the examination with the image information.

Further, the image-related information may be associated with the capture information indicating that the user captured the image using the endoscope. Thus, the user can easily view the captured image later. Note that examples of the capture detection method include a method of detecting that the same image (or images with little change) has continued for a preset number of times, a method of detecting that the same image has continued for a preset period, and a method of detecting that a snapshot has been taken.

Further, the image-related information may be associated with the adjustment history information indicating that the color and volume of the detection range display made by the user during the examination were adjusted.

Subsequently, the examination screen generation unit 7 obtains the image information, the analysis information, and the user setting information, and generates the output information for outputting the examination screen (the image, the sound, and the like) to the output device 24 on the basis of the obtained image information, analysis information, and user setting information (step B3).

Specifically, in step B3, the examination screen generation unit 7 generates the output information for displaying the examination screen 61 as illustrated in FIG. 6 on the display of the output device 24. Further, in step B3, the examination screen generation unit 7 generates the output information for output from the speaker of the output device 24.

Note that when the user is the doctor and shows and explains the examination screen to the patient during the examination, in order to make the color easy for the patient to understand, the user changes the color by using the color adjustment unit 64. Further, when the sound is not required in the case of explanation, the volume adjustment unit 65 is used to minimize the volume.

Note that the order of processing in step B2 and step B3 may be reversed.

Subsequently, the examination management information generation unit 5 determines whether or not the end information indicating the end of the examination has been obtained (step B4). If the end information has been obtained (step B4: Yes), the process proceeds to step B5. If the end information has not been obtained (step B4: No), the process proceeds to step B2 and the processes of steps B2 and B3 are continued.

Specifically, in step B4, when the user determines that the examination is completed, the examination end display 66 on the examination screen 61 displayed on the display of the output device 24 is selected by the user, and the end information is output to the examination management information generation unit 5.

Subsequently, the examination management information generation unit 5 generates the examination management information by associating the plurality of pieces of image-related information generated during the examination period with the examination information indicating the period during which the examination is currently being performed (step B5).

Specifically, in step B5, the examination management information generation unit 5 generates the examination management information by associating the plurality of pieces of image-related information generated during the examination period with the examination information indicating the period during which the examination is currently being performed. Subsequently, in step B5, the examination management information generation unit 5 stores the generated examination management information in the storage device.

When the examination result is displayed on the output device 24 after the examination is completed, the examination result screen generation unit 8 obtains the examination management information from the storage device and outputs the image, the sound, or the like to the output device 24. Specifically, the examination result screen generation unit 8 generates the output information for displaying the examination result screen 81 as illustrated in FIG. 8 on the display of the output device 24. Further, the examination result screen generation unit 8 generates, for example, the output information for output from the speaker of the output device 24.

Note that after the examination is completed, the adjustment made during the examination may be fed back to automatically change the profile settings. For example, the profile setting may be changed on the basis of the adjustment history information included in the image-related information described above.

Effect of the Present Example Embodiment

As described above, according to the present example embodiment, the image-related information including the image information, the analysis information, and the user information can be managed for each examination, and therefore the user can efficiently use the image information and the analysis information after the examination.

[Program]

A program in the example embodiment of the present invention may be any program that causes a computer to execute steps A1 and A2 illustrated in FIG. 9 and steps B1 to B5 illustrated in FIG. 10. By installing and executing the program on the computer, the endoscopy support apparatus and the endoscopy support method in the present example embodiment can be implemented. In this case, a processor of the computer functions as the analysis information generation unit 2, the user information generation unit 3, the image-related information generation unit 4, the examination management information generation unit 5, the user setting information generation unit 6, the examination screen generation unit 7, and the examination result screen generation unit 8, and performs processing.

Further, the program in the present example embodiment may be executed by a computer system constructed by a plurality of computers. In this case, for example, each computer may function as any of the analysis information generation unit 2, the user information generation unit 3, the image-related information generation unit 4, the examination management information generation unit 5, the user setting information generation unit 6, the examination screen generation unit 7, and the examination result screen generation unit 8.

[Physical Configuration]

Figure 11:
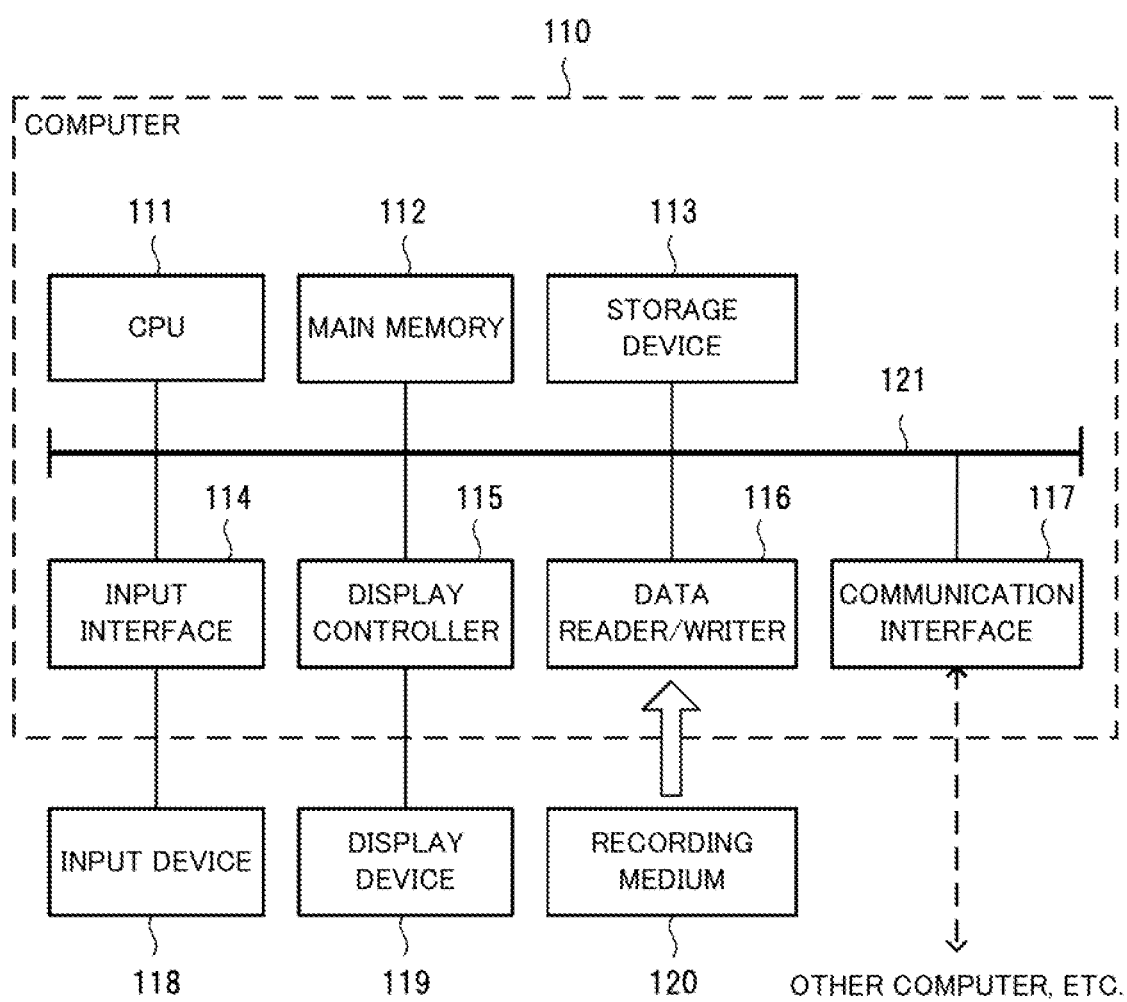
FIG. 11 is a diagram illustrating an example of a computer for realizing the endoscopy support apparatus.

Here, a computer for implementing the endoscopy support apparatus by executing the program in the example embodiment will be described with reference to FIG. 11. FIG. 11 is a block diagram illustrating an example of the computer for implementing the endoscopy support apparatus in the example embodiment of the present invention.

As illustrated in FIG. 11, a computer 110 includes a central processing unit (CPU) 111, a main memory 112, a storage device 113, an input interface 114, a display controller 115, a data reader/writer 116, and a communication interface 117. These parts are connected to each other via a bus 121 so as to be capable of data communication. Note that the computer 110 may include a graphics processing unit (GPU) or a field-programmable gate array (an FPGA) in addition to the CPU 111 or in place of the CPU 111.

The CPU 111 expands the program (code) in the present example embodiment stored in the storage device 113 into the main memory 112 and executes the program in a predetermined order to perform various operations. The main memory 112 is typically a volatile storage device such as a dynamic random access memory (DRAM). Further, the program in the present example embodiment is provided in a state of being stored in a computer-readable recording medium 120. The program in the present example embodiment may be distributed on the Internet connected via the communication interface 117. Note that the recording medium 120 is a non-volatile recording medium.

Further, examples of the storage device 113 include a semiconductor storage device such as a flash memory in addition to a hard disk drive. The input interface 114 mediates data transmission between the CPU 111 and an input device 118 such as a keyboard and a mouse. The display controller 115 is connected to a display device 119 and controls display on the display device 119.

The data reader/writer 116 mediates the data transmission between the CPU 111 and the recording medium 120, reads the program from the recording medium 120, and writes a processing result in the computer 110 to the recording medium 120. The communication interface 117 mediates the data transmission between the CPU 111 and another computer.

Further, examples of the recording medium 120 include a general-purpose semiconductor storage device such as a compact flash (CF) (registered trademark) and a secure digital (SD), a magnetic recording medium such as a flexible disk, or an optical recording medium such as a compact disk read only memory (CD-ROM).

Note that the endoscope examination apparatus 1 in the present example embodiment can also be implemented by using hardware corresponding to each part instead of the computer in which the program is installed. Further, the endoscope examination apparatus 1 may be partially implemented by a program and the rest may be implemented by hardware.

[Supplementary Note]

Regarding the above example embodiment, the following supplementary notes will be further disclosed. A part or all of the above-described example embodiment can be described by (Supplementary note 1) to (Supplementary note 12) described below, but it is not limited to the following descriptions.

(Supplementary Note 1)

An endoscopy support apparatus including:
an analysis information generation unit configured to input image information of an imaged living body into a model, estimate a region of a target site of the living body, and generate analysis information including region information indicating the estimated region and score information indicating likeness of the region to the target site;
a user information generation unit configured to generate user information related to a user, which has been input by the user using a user interface;
an image-related information generation unit configured to generate image-related information by associating imaging date and time information indicating a date and time when an image was captured, the analysis information, and the user information, for each piece of image information; and
an examination management information generation unit configured to generate examination management information by associating a plurality of pieces of the image-related information with examination information indicating an examination period.

(Supplementary Note 2)

The endoscopy support apparatus described in supplementary note 1, including a user setting information generation unit configured to generate user setting information used for setting output of the analysis information for each user.

(Supplementary Note 3)

The endoscopy support apparatus described in supplementary note 2, in which the user setting information includes at least one of setting information for changing display of the region according to the score information and setting information for changing a volume according to the score information, in an examination.

(Supplementary Note 4)

The endoscopy support apparatus described in any one of supplementary notes 1 to 3, in which when the examination management information generation unit obtains end information indicating an end of the examination, the examination management information generation unit generates the examination management information.

(Supplementary Note 5)

An endoscopy support method including:
inputting image information of an imaged living body into a model, estimating a region of a target site of the living body, and generating analysis information including region information indicating the estimated region and score information indicating likeness of the region to the target site;
generating user information related to a user, which has been input by the user using a user interface;
generating image-related information by associating imaging date and time information indicating a date and time when an image was captured, the analysis information, and the user information, for each piece of image information; and generating examination management information by associating a plurality of pieces of the image-related information with examination information indicating an examination period.

(Supplementary Note 6)

The endoscopy support method described in supplementary note 5, including generating user setting information used for setting output of the analysis information for each user.

(Supplementary Note 7)

The endoscopy support method described in supplementary note 6, in which the user setting information includes at least one of setting information for changing display of the region according to the score information and setting information for changing a volume according to the score information, in an examination.

(Supplementary Note 8)

The endoscopy support method described in any one of supplementary notes 5 to 7, in which when end information indicating an end of the examination is obtained, the examination management information is generated.

(Supplementary Note 9)

A computer readable recording medium including a program recorded thereon, the program including instructions for causing a computer to carry out:

inputting image information of an imaged living body into a model, estimating a region of a target site of the living body, and generating analysis information including region information indicating the estimated region and score information indicating likeness of the region to the target site;

generating user information related to a user, which has been input by the user using a user interface;

generating image-related information by associating imaging date and time information indicating a date and time when an image was captured, the analysis information, and the user information, for each piece of image information; and generating examination management information by associating a plurality of pieces of the image-related information with examination information indicating an examination period.

(Supplementary Note 10)

The computer readable recording medium described in supplementary note 9 including a program recorded thereon, the program including instructions that cause a computer to carry out generating user setting information used for setting output of the analysis information for each user.

(Supplementary Note 11)

The computer readable recording medium described in Supplementary note 10, in which the user setting information includes at least one of setting information for changing display of the region according to the score information and setting information for changing a volume according to the score information, in an examination.

(Supplementary Note 12)

The computer readable recording medium described in any one of Supplementary notes 9 to 11, in which when end information indicating an end of the examination is obtained, the examination management information is generated.

Although the present invention has been described above with reference to the example embodiment, the present invention is not limited to the above example embodiment. Various changes that can be understood by those skilled in the art can be made within the scope of the present invention in terms of the structure and details of the present invention.

INDUSTRIAL APPLICABILITY

As described above, according to the present invention, it is possible to organize a large number of living body internal images obtained during the examination period and their image analysis results, for each examination. The present invention is useful in fields where management of a large number of images is required.

REFERENCE SIGNS LIST

1 Endoscopy support apparatus
2 Analysis information generation unit
3 User information generation unit
4 Image-related information generation unit
5 Examination management information generation unit
6 User setting information generation unit
7 Examination screen generation unit
8 Examination result screen generation unit
20 System
21 Endoscope
22 Control unit
23 User interface
24 Output device
110 Computer
111 CPU
112 Main memory
113 Storage device
114 Input interface
115 Display controller
116 Data reader/writer
117 Communication interface
118 Input device
119 Display device
120 Recording medium
121 Bus

What is claimed is:

1. An endoscopy support apparatus comprising:
a processor; and
a memory storing instructions executable by the processor to:
input a plurality of pieces of image information of a living body imaged by an endoscope into a model;
for each piece of image information, estimate a region of a target site of the living body, and generate analysis information including region information indicating the estimated region and score information indicating a likeness of the region to the target site;
generate user information related to a user, which has been input by the user using a user interface;
generate image-related information by associating imaging date and time information indicating a date and time when an image was captured, the analysis information, and the user information, for each piece of image information;
generate examination management information by associating the image-related information generated for each piece of image information during an examination period with examination information identifying an examination;
cause a display of an output device to display an examination result screen indicating an examination result based on the examination management information;

classify the score information for each piece of image information that lies within a score range set by the user via the examination result screen; and cause the display to display the examination information, the piece of image information, the imaging date and time information, and the analysis information, for each piece of image information for which the score has been classified.

2. The endoscopy support apparatus according to claim 1, wherein the instructions are executable by the processor to further:

generate user setting information used for setting output of the analysis information for each of a plurality of users.

3. The endoscopy support apparatus according to claim 2, wherein the user setting information includes at least one of setting information for changing display of the region according to the score information and setting information for changing a volume according to the score information, in the examination.

4. The endoscopy support apparatus according to claim 1, wherein when the processor obtains end information indicating an end of the examination, the processor generates the examination management information.

5. An endoscopy support method performed by a computer and comprising:

inputting a plurality of pieces of image information of a living body imaged by an endoscope into a model;

for each piece of image information, estimating a region of a target site of the living body, and generating analysis information including region information indicating the estimated region and score information indicating a likeness of the region to the target site;

generating user information related to a user, which has been input by the user using a user interface;

generating image-related information by associating imaging date and time information indicating a date and time when an image was captured, the analysis information, and the user information, for each piece of image information;

generating examination management information by associating the image-related information generated for each piece of image information during an examination period with examination information identifying an examination;

causing a display of an output device to display an examination result screen indicating an examination result based on the examination management information;

classifying the score information for each piece of image information that lies within a score range set by the user via the examination result screen; and causing the display to display the examination information, the piece of image information, the imaging date and time information, and the analysis information, for each piece of image information for which the score has been classified.

6. The endoscopy support method according to claim 5, further comprising generating user setting information used for setting output of the analysis information for each of a plurality of users.

7. The endoscopy support method according to claim 6, wherein the user setting information includes at least one of setting information for changing display of the region according to the score information and setting information for changing a volume according to the score information, in the examination.

8. The endoscopy support method according to claim 5, wherein when end information indicating an end of the examination is obtained, the examination management information is generated.

9. A non-transitory computer readable recording medium storing a program including instructions that cause a computer to carry out:

inputting a plurality of pieces of image information of a living body imaged by an endoscope into a model;

for each piece of image information, estimating a region of a target site of the living body, and generating analysis information including region information indicating the estimated region and score information indicating a likeness of the region to the target site;

generating user information related to a user, which has been input by the user using a user interface;

generating image-related information by associating imaging date and time information indicating a date and time when an image was captured, the analysis information, and the user information, for each piece of image information;

generating examination management information by associating the image-related information generated for each piece of image information during an examination period with examination information identifying an examination;

causing a display of an output device to display an examination result screen indicating an examination result based on the examination management information;

classifying the score information for each piece of image information that lies within a score range set by the user via the examination result screen; and causing the display to display the examination information, the piece of image information, the imaging date and time information, and the analysis information, for each piece of image information for which the score has been classified.

10. The non-transitory computer readable recording medium according to claim 9, wherein the instructions further cause the computer to carry out generating user setting information used for setting output of the analysis information for each of a plurality of users.

11. The non-transitory computer readable recording medium according to claim 10, wherein the user setting information includes at least one of setting information for changing display of the region according to the score information and setting information for changing a volume according to the score information, in the examination.

12. The non-transitory computer readable recording medium according to claim 9, wherein when end information indicating an end of the examination is obtained, the examination management information is generated.

13. The endoscopy support apparatus according to claim 1, wherein the model is generated by machine learning, and the examination result is optimized for the user based on a user profile included in the user information.

14. The endoscopy support method according to claim 6, wherein the model is generated by machine learning, and
the examination result is optimized for the user based on a user profile included in the user information.

15. The non-transitory computer readable recording medium according to claim 9, wherein the model is generated by machine learning, and
the examination result is optimized for the user based on a user profile included in the user information.

\* \* \* \* \*